United States Patent [19]

Vlasich

[11] Patent Number: 4,641,766

[45] Date of Patent: Feb. 10, 1987

[54] METERING DISPENSER FOR HIGH VISCOSITY COMPOSITIONS

[75] Inventor: Richard J. Vlasich, Fort Worth, Tex.

[73] Assignee: Alcon Laboratories, Inc., Fort Worth, Tex.

[21] Appl. No.: 667,624

[22] Filed: Nov. 2, 1984

[51] Int. Cl.$^4$ .............................................. B67D 5/42
[52] U.S. Cl. .................................. 222/391; 74/141.5; 433/89; 604/223
[58] Field of Search ....................... 222/391, 386, 390; 604/223–224, 227–229, 233; 433/89–90, 81; 401/172–174; 74/141.5, 142, 169

[56] References Cited

U.S. PATENT DOCUMENTS

| | | | |
|---|---|---|---|
| 2,541,949 | 2/1951 | Thacker et al. | 222/391 X |
| 4,189,065 | 2/1980 | Herold | 222/46 |
| 4,299,337 | 11/1981 | Lassmann et al. | 222/391 X |
| 4,416,397 | 11/1983 | Brown | 222/219 |
| 4,456,450 | 6/1984 | Heling | 222/391 X |

Primary Examiner—Charles A. Marmor
Attorney, Agent, or Firm—Lowe, Price, Leblanc, Becker & Shur

[57] ABSTRACT

A dispensing device including a hollow cylindrical body from which a high viscosity composition is discharged in precisely metered doses by a plunger rod longitudinally movable within the body. A series of projection are formed at equispaced, longitudinal intervals from each other on the plunger rod. A pair of parallel actuating arms pivotally mounted on the body extend along opposite side of the plunger rod and are formed with a pair of teeth, respectively, projecting inward toward the rod. By depressing the arms, the teeth pivot into engagement with one of the projections to advance the plunger within the body to expel a desired amount of composition. In a preferred embodiment, advancement of the plunger rod through a precise distance is automatically controlled via contact between the teeth with stop surfaces formed on the next in-line projection.

11 Claims, 5 Drawing Figures

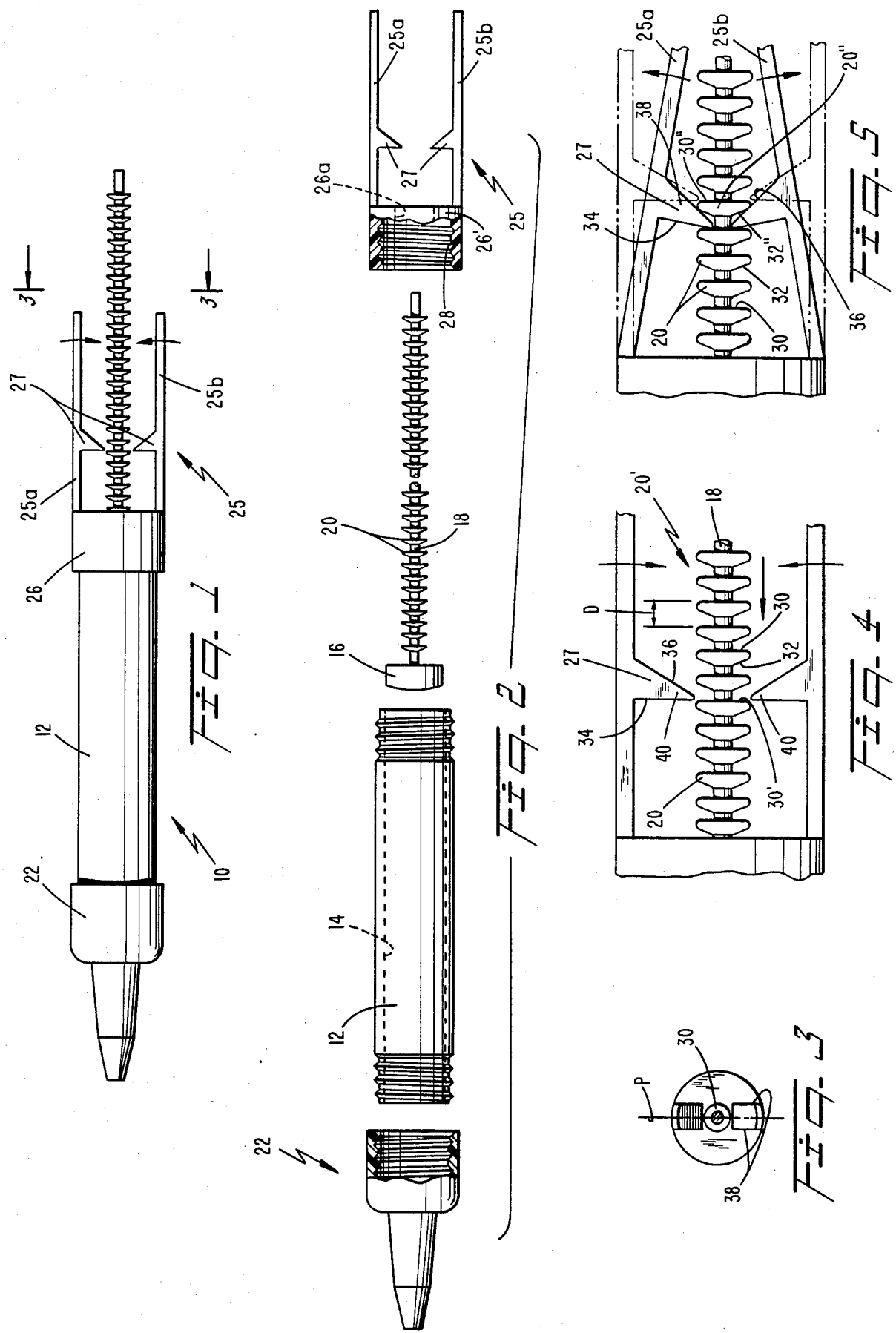

METERING DISPENSER FOR HIGH VISCOSITY COMPOSITIONS

TECHNICAL FIELD

The present invention relates generally to dispensing devices and, more particularly, to a dispensing device for metering precise doses of high viscosity or gel-like compositions.

BACKGROUND ART

There exists a need for dispensing in precisely metered amounts various types of high viscosity or gel-like medicinal and dental compositions, such as Pilocarpine which is an anti-glaucoma agent normally dispensed in doses as small as 10 to 15 μl.

One type of dispenser capable of dispensing the aforesaid composition comprises an elongate hollow body from which the composition can be metered through a closable discharge opening by longitudinally advancing a piston within the body attached to a threaded spindle. The spindle engages a nut mounted on a rear end of the body. A flange provided on the nut has indicia cooperating with an orientation wing mounted to rotate the spindle. The amount of composition to be dispensed is controlled by the user who rotates the wing into registration with one of the indicia displayed on the flange.

As the amount of dispensed composition is controlled by user sight alignment between the orientation wing and indicia, the metering accuracy is dependent on how exact the wing is set to the respective indicia. Accurate metering thus requires careful handling of the device. There is also a chance of the spindle being screwed out of the hollow body due to careless handling, inadvertent actuation or shock, resulting in an amount of composition corresponding to only an incomplete revolution being dispensed during subsequent rotation of the spindle.

Another problem associated with the foregoing device is that one hand is required to rotate the spindle while the other hand holds the body to dispense the composition. Two handed operation can be cumbersome and particularly difficult for arthritic persons.

To accurately dispense a desired amount of high viscosity composition, U.S. Pat. No. 4,189,065 to Herold discloses a dispensing device wherein a hollow cylindrical body containing composition is formed with a stationary detent engageable with a longitudinal groove provided on a threaded spindle to precisely control the degree of angular rotation of the spindle when rotating a knob mounted thereon to dispense the composition. While this type of device provides greater metering accuracy than the aforementioned dispenser, two handed operation is still required to discharge composition, one hand grasping the body while the other hand rotates the knob. Also, since the detent is a resilient member, it is possible for the groove to overtravel slightly past the detent during rotation of the spindle, due to the resiliency of the latter, causing an excessive amount of composition to be discharged from the dispenser.

It is accordingly an object of the present invention to provide an improved metering dispenser for high viscosity compositions which allows precise metering utilizing simple means.

A further object of the invention is to provide a device achieving exact metering by utilizing a mechanism capable of single-handed operation.

It is another object to provide a device for dispensing high viscosity compositions which precisely controls metering by automatically stopping advancement of a plunger means after a precise amount of composition has been dispensed in one of the embodiments of the invention.

Still a further object is to provide a metering dispenser which is easy to manufacture and safe to handle.

DISCLOSURE OF INVENTION

A device for dispensing high viscosity compositions, in accordance with the present invention, comprises an elongate hollow body having a discharge opening at a front end thereof and a chamber for containing the composition. A plunger rod having a piston slidably received within the hollow body projects through a rear end thereof. In response to longitudinal advancement of the plunger rod, the piston is advanced through the chamber to dispense a predetermined amount of composition through the discharge opening. An actuator or trigger is fixed to the hollow body to engage and longitudinally advance the plunger rod a predetermined incremental distance within the body for precise metering to occur.

The plunger rod is preferably formed with a plurality of longitudinally spaced projections. The actuator includes a pair of actuating arms pivotally secured to the hollow body. The arms extend generally parallel to each other along opposite sides of the plunger rod and are formed with a pair of teeth respectively mounted in opposition to each other. By depressing both arms together, the teeth pivot into engagement with one of the projections to longitudinally advance the plunger rod in the direction of the hollow body to dispense composition.

In accordance with one embodiment of the invention, each projection is formed as a disc-shaped element having a rear, annular abutment surface which the teeth contact to longitudinally advance the rod. Each disc-shaped projection has a front conical surface that is advanced into contact with a respective tooth when the arms are fully depressed to automatically prevent further longitudinal advancement of the plunger rod and precisely index the next in-line projection into the operative position to dispense a successive dose.

In this embodiment, each tooth is preferably of triangular cross-section, when viewed in a plane passing through the actuating arms and a plunger rod, and includes a front surface extending co-planar with each other and generally parallel to the annular abutment surfaces. A rear surface of each tooth is inclined and intersects the associated front surface to establish therewith an apex directed inwardly towards the plunger rod so that depressing the arms together causes each apex to pivot inwardly into contact with the abutment surface of an in-line projection while moving forwardly to longitudinally advance the rod. The inclined rear surfaces of the teeth are arranged to wedge into contact with the front conical surface of the next in-line projection to prevent further advancement of the rod beyond the predetermined distance. The front surfaces of the teeth preferably extend generally orthogonal to the longitudinal axis of the plunger rod.

In accordance with another embodiment of the invention, the actuating arms extend from a threaded mounting sleeve adapted for threaded engagement with an exterior thread formed on the rear end of the hollow body. The rear end of the mounting sleeve is open to permit uninterrupted travel of the plunger rod through the sleeve.

The sleeve and actuating arms preferably constitute an integral structure. The plunger rod and cylindrical hollow body are preferably separate structures that can be easily disassembled for cleaning.

Still other objects and advantages of the present invention will become readily apparent to those skilled in this art from the following detailed description, wherein I have discussed only a preferred embodiment of the invention, simply by way of illustration of the best mode contemplated by me for carrying out my invention. As will be realized, the invention is capable of modifications in various obvious respects, all without departing from the invention. For example, various types of spaced projections on the plunger may be utilized, such as separate grooves extending around the plunger or grooves extending across a flat surface on opposite sides of the plunger. Similarly, various types of teeth may be utilized on the actuator, so long as the teeth are capable of engaging the corresponding projections on the plunger to longitudinally advance the plunger rod a predetermined incremental distance within the body of the dispensing device. Accordingly, the drawing and following description are to be regarded as illustrative in nature, and not as restrictive.

BRIEF DESCRIPTION OF THE DRAWING

FIG. 1 is a side elevational view of a metering dispenser for high viscosity compositions in accordance with the present invention;

FIG. 2 is an exploded, sectional view of the various components of the invention in FIG. 1;

FIG. 3 is a sectional view taken along the line 3—3 of FIG. 1;

FIG. 4 is an enlarged partial elevational view showing the positioning of the actuator teeth with respect to the projections formed on the plunger rod prior to depressing the teeth into contact with an in-line projection to longitudinally advance the piston within the hollow body; and FIG. 5 is a view similar to FIG. 4 showing the actuator teeth depressed into contact with the rear abutment surface of an in-line projection to advance the piston within the hollow body a predetermined distance.

BEST MODE FOR CARRYING OUT THE INVENTION

Referring to FIGS. 1 and 2, metering dispenser 10 of the invention comprises a hollow, cylindrical body 12 having a chamber 14 in which a gel-like composition is contained. A piston 16 slidable within chamber 14 is fixed to the front end of a plunger rod 18. The rod 18 is formed with a plurality of disc-shaped projections 20 equispaced from each other by a distance D along the length thereof. The composition is dispensed in precisely metered quantities through an applicator tip 22 threaded to the front end of body 12 by incrementally advancing piston 16 within the chamber in response to longitudinal advancement of rod 18. Such incremental advancement of rod 18 through distance D is accomplished in the unique manner described more fully below by means of a dispensing actuator 25 having a pair of parallel actuating arms 25a and 25b extending along the rod in diametrically opposing positions to each other. Upon squeezing arms 25a, 25b together, a pair of teeth 27 respectively formed thereon pivot to engage one of identical projections 20 to urge the rod 18 forwardly.

Each disc-shaped projection 20 includes a rear annular abutment surface 30 with which each tooth 27 is pressed into contact to advance the rod 18. As best shown in FIG. 4, each surface 30 is flat and extends orthogonal to the exterior surface of rod 18. The surfaces 30 are spaced from each other by distance D. Each projection 20 also includes a front, conical surface 32 spaced rearwardly from a rear surface 30 of a forwardly adjacent projection. These facing surfaces 30, 32 together establish with a portion of rod 18 extending therebetween, a notch 20' which teeth 27 enter to contact the rear surface when arms 25a, 25b are depressed.

Each tooth 27 is of triangular cross-section, when viewed in a plane P (see FIG. 3) passing through both arms 25a, 25b and rod 18, and includes a front surface 34, a rear inclined surface 36, and parallel triangular side surfaces 38. Front surfaces 34 extend co-planar with each other and parallel to abutment surfaces 30. The rear inclined surface 36 intersects its associated front surface 34 to establish therewith an apex portion 40 directed inwardly towards projections 20. By squeezing arms 25a, 25b together, both apex portions 40 pivot into contact with the rear surface of an in-line projection 20 to advance the rod.

The arms 25a, 25b of dispensing actuator 25 are formed integral with a cylindrical mounting sleeve 26 having internal threads 28 engageable with the rear exterior threaded end of body 12. The sleeve 26 is also formed with a rear wall 26' having an opening 26a through which plunger rod 18 projects rearwardly when actuator 25 is fixed to body 12. When chamber 14 is completely filled with high viscosity composition, piston 16 abuts against the inner surface of rear wall 26'. The entire length of plunger rod 18 projects rearwardly through opening 26a (see FIG. 1 position), automatically and intially positioning one of projections 20 in an operative, in-line position with respect to teeth 27. This in-line position is shown in FIG. 4, wherein front surfaces 34 of teeth 27 are positioned slightly behind and parallel to the rear abutment surface 30 of one of projections 20.

In this initial, operative position shown in FIG. 4, as arms 25a, 25b are initially squeezed together, the tips of apex portions 40 pivot into initial contact with the outer peripheral edge of an in-line abutment surface 30'. As arms 25a, 25b are further depressed, this pressing contact transmits a forwardly directed force from teeth 27 against in-line surface 30', due to pivotal movement of the teeth with respect to sleeve 26, causing the surface 30' to yield and begin to advance longitudinally thereby advancing the plunger 40d and piston 16 within chamber 14 to dispense composition. In addition to imparting a forwardly directed force against surface 30', the contact tips of apex portions 40 also begin to slide radially inward along the surface 30' toward the exterior surface of the plunger rod. While advancing in the radial direction, teeth 27 apply a constant forward force to longitudinally advance the plunger rod.

As the in-line abutment surface 30' is advanced by teeth 27 through distance D, the rear inclined surface 36 pivots inwardly into contact with front conical surface 32" of the next in-line projection 20" as shown in FIG. 5. This conical surface 32" is arranged to make a wedging contact with the rear tooth surface 36 in cooperation with the tips of apex portions 40 pivoting into contact with the exterior surface of rod 18 to prevent further advancement of the plunger rod past distance D even if the user further attempts to depress arms 25a, 25b together.

In accordance with the invention, actuation of dispensing actuator 25 for precise metering of composition is easily accomplished by the user with one hand, simply by placing the palm and fingers of the hand (not shown) so that the thumb and index fingers respectively rest upon actuating arms 25a, 25b to squeeze the arms together by application of slight pressure. This allows the invention to dispense certain compositions, such as pilocarpine, directly onto desired areas of the body, e.g., the eyes. Since teeth 27 are automatically restrained from further advancing rod 18 once the rod has advanced the distance D because of the aforesaid wedging contact, and because the amount of composition dispensed with each incremental advancement of the plunger is defined by the constant inner diameter of body 12, dispensing of an accurately metered amount of composition is always assured.

As the in-line abutment surface 30' is advanced by teeth 27 to its FIG. 5 final position, it will be appreciated that the next in-line abutment surface 30" automatically advances into the initial position shown in FIG. 4 (see also phantom line position of teeth 27 in FIG. 5), permitting successive doses of composition to be dispensed through applicator tip 22.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment is chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A device for dispensing predetermined doses of high viscosity compositions, comprising:
    (a) an elongate hollow body having a discharge opening at a front end thereof and an interior region for containing said composition;
    (b) plunger means received within said hollow body through a rear end thereof for dispensing said composition through the front end in response to longitudinal advancement of said plunger means through the body; and
    (c) actuating means fixed to said hollow body for engaging with and to longitudinally advance said plunger means a predetermined incremental distance within the body, causing a precisely metered amount of composition to be dispensed through the discharge opening, said actuating means including a pair of actuating arms each having one end secured to said hollow body and an opposite free end projecting rearwardly from said hollow body and the front end thereof, said arms including, intermediate said one ends and free ends thereof, means for engaging said plunger means to longitudinally advance same through the body upon depressing of said free ends together.

2. The device of claim 1, wherein said plunger means includes a plunger rod and a piston fixed to a front end thereof in sliding contact with inner walls of the hollow body to expel composition through the discharge opening during advancement of said piston through said region.

3. The device of claim 2, wherein said plunger rod is formed with a plurality of longitudinally spaced projections, said actuating arms being pivotally secured to the hollow body and extending generally parallel to each other along opposite sides of the plunger rod, said arms including a pair of teeth respectively formed thereon in opposition to each other, depressing both arms together causes the teeth to engage one of said projections to longitudinally advance the plunger rod in the direction of the hollow body so that composition is dispensed through the discharge opening.

4. The device of claim 3, wherein each projection is formed with a rear annular abutment surface, said teeth being formed intermediate opposite ends of said arms and arranged to pivot into contact with the abutment surface of one of the projections operatively positioned adjacent the teeth to advance the rod forwardly a predetermined distance, thereby advancing the next in-line projection into operative position to dispense a successive dose.

5. The device of claim 4, wherein said rear abutment surfaces of the projection are equispaced from each other by said predetermined distance.

6. The device of claim 5, wherein each projection is disc-shaped, and includes a front conical surface, and each tooth is of triangular cross-section, when viewed in a plane passing through the actuating arms and plunger rod.

7. The device of claim 6, wherein each tooth has a front surface extending co-planar with each other and generally parallel to said annular abutment surfaces is an undepressed state of said actuating arms, and a rear inclined surface intersecting an associated front surface to establish therewith an apex directed inwardly toward the plunger rod so that depressing of said actuating arms together causes each apex to pivot inwardly into contact with the abutment surface of an in-line projection while moving forwardly to longitudinally advance the plunger rod, said conical surface of a next in-line projection being arranged to make a wedging contact with the rear tooth surface when said plunger rod has advanced the predetermined distance to thereby prevent further advancement of the rod and assure that the next in-line abutment surface is operatively positioned to dispense a successive dose of composition.

8. The device of claim 7, wherein the front surface of said tooth extends generally orthogonal to the longitudinal axis of the plunger rod in an undepressed state of said actuating arms.

9. The device of claim 3, wherein said actuating arm extends from a threaded mounting sleeve adapted for threaded engagement with an exterior thread formed on the rear end of the hollow body.

10. The device of claim 9, wherein a rear end of said mounting sleeve is open to permit passage therethrough of said plunger rod.

11. The device of claim 1, further including an applicator tip in threaded engagement with the front end of the hollow body.

* * * * *